United States Patent [19]

Lin

[11] Patent Number: 5,370,663
[45] Date of Patent: Dec. 6, 1994

[54] IMPLANTABLE CARDIAC-STIMULATOR WITH FLAT CAPACITOR

[75] Inventor: Jack H. Z. Lin, Lake Jackson, Tex.

[73] Assignee: Intermedics, Inc., Angleton, Tex.

[21] Appl. No.: 105,836

[22] Filed: Aug. 12, 1993

[51] Int. Cl.$^5$ ............................................. A61N 1/39
[52] U.S. Cl. ................................................ 607/5; 607/36
[58] Field of Search ............................ 607/5, 36, 115; 361/303, 308.1–308.3, 297

[56] References Cited

U.S. PATENT DOCUMENTS

| 965,992 | 8/1910 | Dean | 361/303 X |
|---|---|---|---|
| 3,622,847 | 11/1971 | Grahame | 361/303 X |
| 3,987,799 | 10/1976 | Purdy et al. | 607/36 |
| 4,254,755 | 3/1981 | Langer | 607/5 |
| 4,481,558 | 11/1984 | Endoh et al. | 361/303 |
| 5,131,388 | 7/1992 | Pless et al. | |
| 5,241,960 | 9/1993 | Anderson et al. | 607/5 |

Primary Examiner—Lee S. Cohen
Assistant Examiner—Jeffrey R. Jastrzab
Attorney, Agent, or Firm—Richard L. Robinson

[57] ABSTRACT

An implantable cardiac defibrillator includes a housing having a thickness dimension that is smaller than either of the length and width dimensions of the housing. Within the housing is an energy storage capacitor having a thickness dimension that is smaller than either of the length and width dimensions of the capacitor. The capacitor includes a first plate layer, a second plate layer, and a dielectric layer separating the first plate layer and the second plate layer. The first plate, second plate and dielectric layers are arranged spirally about an axis parallel to the thickness axis of the capacitor, with the thickness axis of the capacitor being substantially parallel to the thickness axis of the housing. The capacitor is arranged as an annulus having an open center. A battery is disposed within the open center in the same plane as the capacitor. A circuit board and header are arranged in another plane stacked atop the battery and capacitor.

20 Claims, 2 Drawing Sheets

IMPLANTABLE CARDIAC-STIMULATOR WITH FLAT CAPACITOR

BACKGROUND OF THE INVENTION

1. Field of the Invention

The present invention relates generally to implantable defibrillators and relates more particularly to an improved configuration for a capacitor for use in an implantable defibrillator. The improved configuration permits more efficient packaging of the defibrillator components and a more physiologically desirable shape of the defibrillator housing.

2. Background Information

Implantable defibrillators are implanted in patients who can be identified as being likely to suffer cardiac arrhythmias such as ventricular fibrillation that can cause sudden death. The defibrillator detects the occurrence of ventricular fibrillation and automatically delivers defibrillating therapy. Implantable defibrillators in their most general form include appropriate electrical leads for collecting electrical signals generated by the heart, and for delivering electric shocks to the heart to provide defibrillation therapy. Also included are batteries, energy storage capacitors, and control circuitry connected to the leads, batteries and capacitors for sensing the electrical activity of the heart and for charging the capacitors and triggering the delivery of shocks through the leads. Implantable defibrillators can also include circuitry for providing cardioverting therapy for treating tachycardia, and for providing pacing therapy for treating bradycardia.

Defibrillation therapy generally involves rapid delivery of a relatively large amount of electrical energy to the heart at high voltage. Presently available batteries suitable for use in implantable defibrillators are not capable of delivering such energy levels directly. Consequently, it is customary to provide a high voltage storage capacitor that is charged from the battery via appropriate charging circuitry. To avoid wasting battery energy, the high voltage capacitor is not maintained in a state of charge, but rather is charged during an interval after the need for defibrillation therapy has been identified by the control circuitry, and immediately prior to delivering the shock.

The storage capacitors used in implantable defibrillators typically are required to deliver relatively large amounts of energy, on the order of 30 to 40 joules. With present implantable defibrillator capacitor technology, energy density does not exceed 2 joules per cubic centimeter. Thus, the capacitor is necessarily relatively large and constitutes a significant portion of the volume of the implantable defibrillator. Because of their large size, present implantable defibrillators usually must be implanted in the patient's abdomen.

It would be desirable to provide an implantable defibrillator that is smaller so that it can be implanted comfortably in the pectoral region, just as smaller implantable pacemakers are presently implanted. To accomplish this goal, it will be necessary to provide more efficient packaging of the components of the defibrillator within the defibrillator's housing. In the prior art, it has been proposed to replace the conventional cylindrical aluminum electrolytic "photoflash" capacitors with capacitors employing the same aluminum electrolytic technology, but configured to fit in a defibrillator housing having rounded contours. In particular, U.S. Pat. No. 5,131,388, issued Jul. 21, 1992, proposes an implantable defibrillator having a generally planar housing with curved edges that contains an aluminum electrolytic capacitor comprised of a planar layered structure of anode plates and cathode plates, wherein the plane of the anode and cathode plates is generally parallel to the plane of the housing. Such a configuration permits the capacitor to be shaped to conform to the curved edges of the housing and to partially surround other components, such as the batteries.

One consequence of such a layered structure is that the anode and cathode are each comprised of a multiplicity of individual plates which must be electrically connected in common via a multiplicity of individual electrical connections. In contrast, conventional cylindrical aluminum electrolytic capacitors are comprised of a continuous anode plate and a continuous cathode plate rolled spirally into a cylinder, with only a single electrical connection to each plate. I believe that the spiral construction is more easily manufactured because of the smaller number of electrical connections. I have therefore invented an improved configuration for a storage capacitor for an implantable defibrillator that permits more efficient packaging of the capacitor within the housing of the defibrillator and that permits a more physiologically advantageous shape for the defibrillator housing, while retaining the manufacturing advantages of more conventional capacitor construction.

SUMMARY OF THE INVENTION

My invention involves an implantable defibrillator containing a storage capacitor of novel orientation and configuration. The capacitor is "flat" in the sense that its thickness is smaller than its length or width, and the thickness axis of the capacitor is parallel to the thickness axis of the defibrillator housing, which is likewise "flat." The plates of the capacitor are spiralwound about an axis parallel to the thickness axes of the capacitor and the housing.

In accordance with one aspect of the present invention, there is provided an implantable cardiac defibrillator including a housing having mutually orthogonal thickness, width and length axes. The housing has a thickness dimension measured along the thickness axis, a width dimension measured along the width axis and a length dimension measured along the length axis. The thickness dimension is smaller than either of the width and length dimensions. An improved energy storage capacitor within the housing has mutually orthogonal thickness, width and length axes. The capacitor has a thickness dimension measured along the thickness axis, a width dimension measured along the width axis and a length dimension measured along the length axis. The thickness dimension of the capacitor is smaller than either of the width and length dimensions of the capacitor. The capacitor further includes a first plate layer, a second plate layer, and a dielectric layer separating the first plate layer and the second plate layer. The first plate, second plate and dielectric layers are arranged spirally about an axis parallel to the thickness axis of the capacitor, where the thickness axis of the capacitor is substantially parallel to the thickness axis of the housing.

In accordance with another aspect of the present invention, the aforementioned energy storage capacitor is constructed as an annulus with a hollow center.

In accordance with another aspect of the invention, a battery or other component of the defibrillator is disposed within the hollow center of the aforementioned annular energy storage capacitor.

In accordance with yet another aspect of the invention, the aforementioned annular energy storage capacitor can be constructed as multiple separate annular capacitors arranged concentrically.

It is an object of the present invention to provide more efficient packaging of a storage capacitor in an implantable defibrillator such that the defibrillator can be smaller and more advantageously shaped than heretofore possible. Other objects and advantages of the present invention will be apparent from the following descriptions of a preferred embodiment with reference to the drawings.

Figure 1:
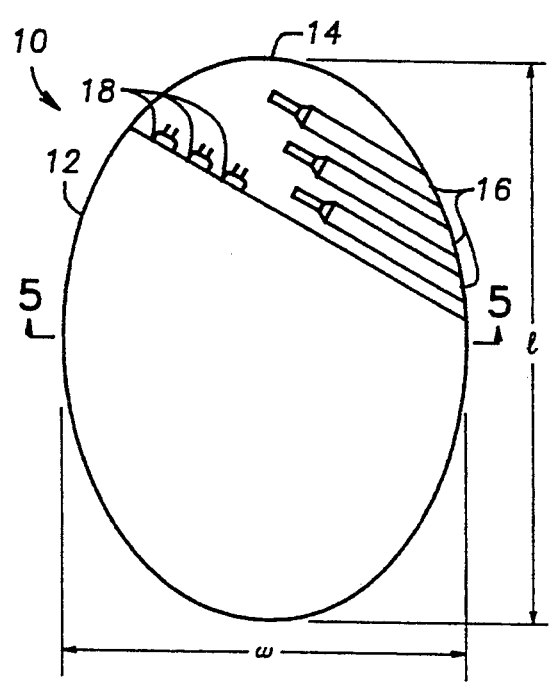
FIG. 1 is a stylized plan view of an implantable defibrillator in accordance with the present invention.
Figure 2:
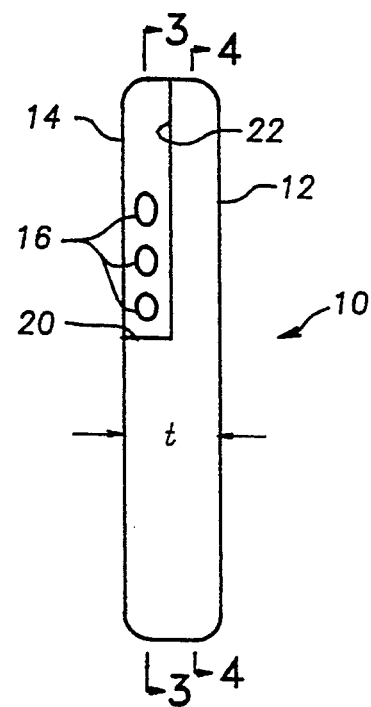
FIG. 2 is a stylized side view of the implantable defibrillator of FIG. 1.
Figure 5:
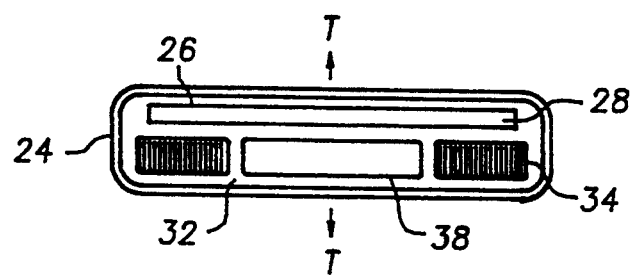
Figure 6:
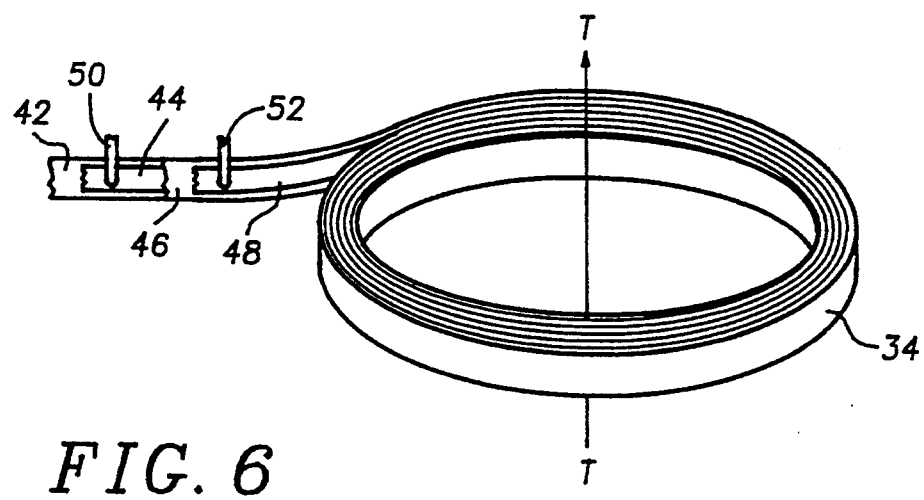
Figure 7:
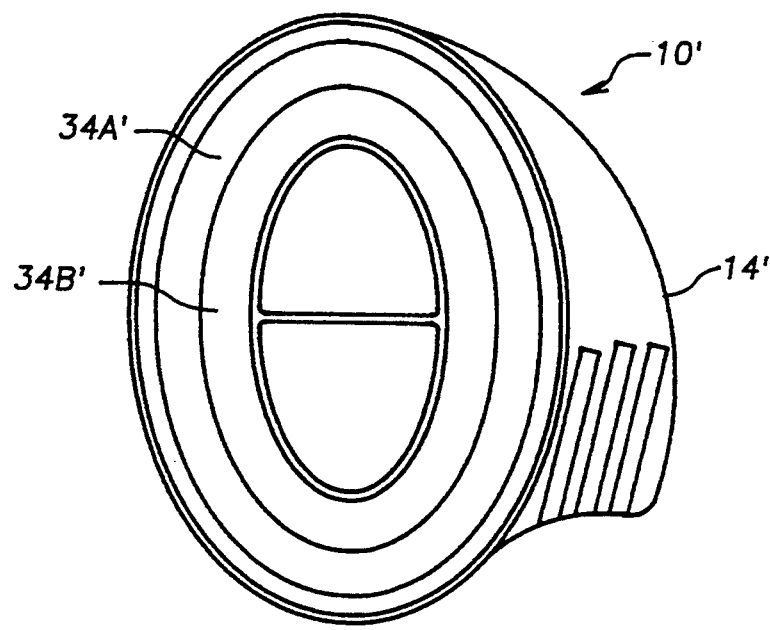

FIG, 4 is a cross-sectional view of the implantable defibrillator of FIG. 1, taken along section plane 4—4 of FIG. 2, and viewed in the direction of the arrows;

FIG. 5 is a cross-sectional view of the implantable defibrillator of FIG. 1, taken along section plane 5—5 of FIG. 1 and viewed in the direction of the arrows;

FIG. 6 is a perspective view of storage capacitor of the implantable defibrillator of FIG. 1, shown partially unwound to reveal the component layers; and FIG. 7 is a cross-sectional view of an alternative embodiment of an implantable defibrillator in accordance with the present invention.

DESCRIPTION OF THE PREFERRED EMBODIMENT

Referring to FIGS. 1 and 2, there is illustrated in stylized fashion an implantable defibrillator 10 constructed in accordance with the present invention. Defibrillator 10 includes an hermetic housing 12 constructed of a biocompatible metal such as titanium, and a transparent cast epoxy header 14 which provides mechanical connection to a plurality of external leads (not shown). Header 14 includes a plurality of ports 16. The proximal end of a lead having one or more electrical contacts is received in each port 16, and makes electrical connection with corresponding electrical contacts (not shown) in header 14. Each electrical contact in header 14 is wired to a corresponding insulated feedthrough 18 which provides an electrical pathway into the interior of hermetic housing 12, for connection to circuitry therein.

Defibrillator 10 is illustrated as being shaped generally as a flat ellipse having a length l, a width w, and a thickness t. Because defibrillator 10 is intended to be implanted surgically in a subcutaneous pocket, where it lies between the dermis and the underlying muscular layers, it is desirable that the thickness dimension t be less than either the length dimension I or the width dimension w. Header 14 occupies approximately one quadrant of the ellipse in the plane defined by the width and length directions, but extends only one-half the thickness dimension t. Thus, the back half of hermetic housing 12 is a full ellipse, whereas the front half of hermetic housing 12 is an ellipse less the portion occupied by header 14. Hermetic housing 12 includes walls 20 and 22 which completely separate the interior of hermetic housing 12 from header 14. In other words, header 14 is cast in place on the surface of housing 12, but does not itself act as a seal.

Figure 3:
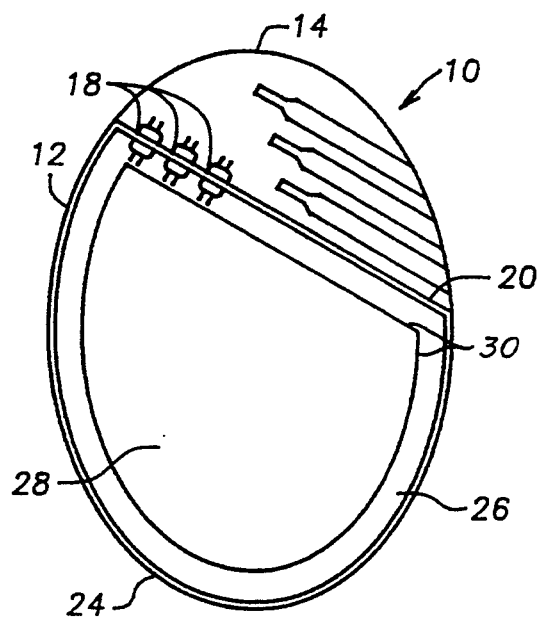
FIG. 3 is a cross-sectional view of the implantable defibrillator of FIG. 1, taken along section plane 3—3 of FIG. 2, and viewed in the direction of the arrows.

Referring to FIG. 3, there is illustrated a cross-sectional view of defibrillator 10 taken along section plane 3—3 of FIG. 2. Hermetic housing 12 includes an outer elliptical wall 24 joined to previously mentioned wall 20 to define a first interior chamber 26 in which is received a circuit board 28 shown in simplified stylized fashion, and having a peripheral edge 30 that generally conforms to the configuration of the outer wall 24 and wall 20. Circuit board 28 contains most of the electrical components of the control circuitry of defibrillator 10. Electrical connections between circuit board 28 and the electrical contacts of header 14 associated with the ports 16 are made via insulated feedthroughs 18. It should be appreciated that header 14 and circuit board 28 lie substantially in the same plane, and occupy complementary portions of the generally elliptical outline of defibrillator 10. Thus, if necessary or desirable, the relative areas occupied by header 14 and circuit board 28 can be altered to accommodate a greater or lesser number of ports 16, or to provide more or less area on circuit board 28 for electrical components.

Figure 4:
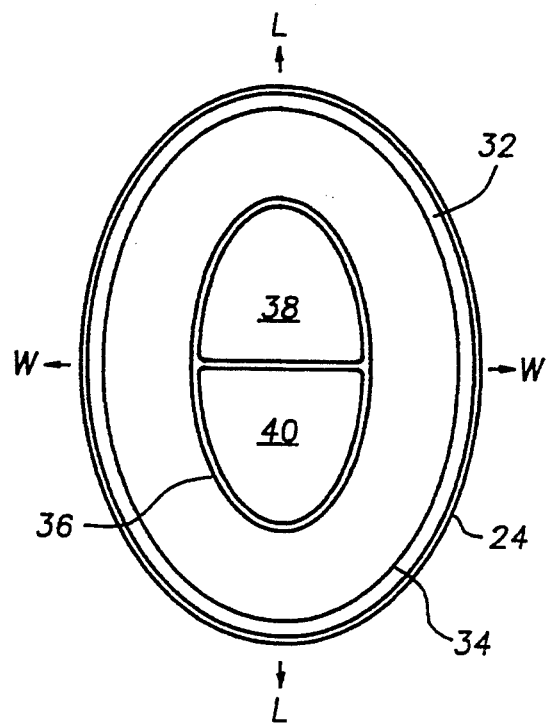

Referring to FIGS. 4 and 5, there is illustrated a cross-sectional view of defibrillator 10 taken along section plane 4—4 of FIG. 2, and a cross-sectional view of defibrillator 10 taken along section plane 5—5 of FIG. 1, respectively. Outer wall 24 defines a second interior chamber 32 that is elliptical in the plane defined by length direction L—L and width direction W—W, and having a thickness approximately half the thickness dimension t of defibrillator 10 measured in the thickness direction T—T. Disposed within chamber 32 is an annular elliptical storage capacitor 34 defining a hollow center area 36. A pair of half-ellipse shaped batteries 38 and 40 are received in center area 36 and are surrounded by capacitor 34. Because first chamber 26 and second chamber 32 communicate over the entire area of chamber 26, electrical connections between circuit board 28 and batteries 38 and 40 and capacitor 34 can be provided easily where desired. It should be appreciated that batteries 38 and 40 and capacitor 34 lie substantially in the same plane and occupy complementary areas of chamber 32. Thus, the design of the configuration of batteries 38 and 40, capacitor 34, and hermetic housing 12 are interrelated. The optimum tradeoff will take into consideration the desired overall size of the defibrillator 10, the desired capacitance of the capacitor 34, and the desired energy capacity of the batteries 38 and 40, recognizing that for a given capacitor or battery technology, capacitance and energy capacity are functions of physical dimension.

Referring to FIG. 6, capacitor 34 is illustrated. The embodiment illustrated utilizes conventional aluminum electrolytic capacitor technology in a novel orientation and configuration. An aluminum electrolytic capacitor can accumulate an electric charge between facing aluminum plates where a dielectric film is formed on the anode plate by anodic oxidation in the presence of a non-aqueous electrolyte. Capacitor 34 includes as principal components a first paper separator layer 42, an aluminum foil cathode plate layer 44, a second paper separator layer 46, and an aluminum foil anode plate layer 48. Lead wire terminals 50 and 52 are mechanically and electrically connected to cathode plate 44 and anode plate 48 respectively. The aforementioned layers 42, 44, 46 and 48 are wound together spirally about an axis parallel to the thickness direction T—T to form overlapping turns, thereby building up a cylindrical capacitor from the inside out. In contrast to prior art cylindrical capacitors, the embodiment illustrated in FIG. 6 is wound about a mandrel or tubular core so as to leave a central opening and to form a cylindrical capacitor of generally annular configuration. The term "cylindrical" is meant to be understood in its geometric sense, i.e., a surface traced by a straight line moving parallel to a fixed straight line and intersecting a fixed curve. The curve can be circular, as in the usual case, or it can be elliptical or oval, or arbitrarily shaped. Thus, in accordance with the present invention, one could form an annular capacitor by winding the plates and separators spirally about a mandrel or tubular core of circular, elliptical, oval, polygonal or other desired cross-section.

The separator paper layers 42, 46 of capacitor 34 are saturated with a known electrolyte as is conventional in the construction of electrolytic capacitors, and thus it is necessary to provide a sealing layer or envelope about the exposed surfaces of the spirally wound capacitor, with the lead wire terminals 50 and 52 extending through the sealing layer to provide electrical access to the anode and cathode plate layers. Any suitable polymeric material that is resistant to the electrolyte can be utilized as the sealing layer, and an appropriate adhesive can be used to seal the points where the lead wire terminals pass through the sealing layer.

A capacitor constructed in accordance with the present invention using conventional aluminum electrolytic capacitor technology is calculated to have the following construction details:

Capacitance: 250 μF
DC working voltage: 375 V
Shape: Elliptical annulus
Length: 8.3 cm
Width: 7.3 cm
Thickness: 6.5 mm
Center opening: 6.7 cm×5.7 cm
Anode foil thickness: 105 μm
Cathode foil thickness: 20 μm
Paper separator thickness: 20 μm Referring in particular to FIGS. 4 and 5, it can be appreciated how the present invention results in very efficient packaging of the large components of an implantable defibrillator. In the layer comprised of capacitor 34 and batteries 38 and 40, there is very little wasted space because of the concentric arrangement of an elliptical battery (in two parts) and the elliptical annular capacitor. In the layer comprised of circuit board 28 and header 14, there is likewise little wasted space because circuit board 28 and header 14 can be designed to selected shaped occupying selected areas of the plane as may be dictated by a well designed arrangement of the small components mounted on each. The efficient packaging arrangement derives in large part from the provision of a "flat" storage capacitor. By the term "flat" it is meant that the thickness of the capacitor is less than either the width or the length of the capacitor, where thickness is measured along the axis about which the plates are spirally arranged. The provision of such a "flat" capacitor in an implantable defibrillator housing that is similarly "flat" permits the defibrillator housing to be small and more advantageously shaped than in the prior art.

Referring in particular to FIG. 7, there is illustrated an alternative embodiment shown in cross-section in the same manner as the cross-sectional view of the first embodiment as shown in FIG. 4. In this alternative embodiment, a header 14' is attached to the periphery of defibrillator 10' rather than in the manner of the first embodiment. Also, rather than a single energy storage capacitor, defibrillator 10' includes two concentric elliptical annular capacitors 34A' and 34B'. Separate concentric annular capacitors 4A' and 34B' are connected in series. This permits each capacitor to be constructed to withstand a voltage that is approximately half the total voltage that must be withstood by the entire capacitor bank, thereby easing the design requirements and enhancing reliability of the capacitors.

Although preferred embodiments have been illustrated and described with respect to aluminum electrolytic capacitor technology, it should be understood that the principles of the present invention can be utilized with other capacitor technology, such as polyethylene or polystyrene film capacitors, for example, wherein flexible anode plates, cathode plates and dielectric layers are wound together in a spiral. It also may be desirable to provide multiple capacitors connected in parallel to increase the total capacitance. Furthermore, the batteries need not be surrounded by the capacitor, as some other major component such as the circuit board may be more advantageously placed within the hollow center of the annular capacitor in a particular defibrillator design. Also, one may desire to provide a multiplicity of smaller capacitors without hollow centers that are arranged side by side in the same "flat" orientation described herein. A plurality of small "flat" hexagonally shaped capacitors could be densely packed together in honey-comb fashion and yet conform well to a curved peripheral edge of a defibrillator housing.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

I claim:

1. In an implantable cardiac stimulator including an electrical contact, a battery, an energy storage capacitor and control circuitry electrically connected to said contact, battery and capacitor, in which said battery, capacitor and control circuitry are disposed within a housing having mutually orthogonal thickness, width and length axes, said housing having a thickness dimension measured along said thickness axis, a width dimension measured along said width axis and a length dimension measured along said length axis, wherein said thickness dimension is smaller than either of said width and length dimensions, the improvement comprising:

said energy storage capacitor having mutually orthogonal thickness, width and length axes, and having a thickness dimension measured along said thickness axis, a width dimension measured along said width axis and a length dimension measured along said length axis, wherein said thickness dimension of said capacitor is smaller than either of said width and length dimensions of said capacitor, said capacitor further including a first plate layer, a second plate layer, and a dielectric layer separating said first plate layer and said second plate layer, said first plate, second plate and dielectric layers being arranged spirally about an axis parallel to said thickness axis of said capacitor, said thickness axis of said capacitor being substantially parallel to said thickness axis of said housing.

2. The implantable cardiac stimulator of claim 1, wherein said first plate, second plate and dielectric layers are generally arranged as an annulus having an open center.

3. The implantable cardiac stimulator of claim 2, in which said battery is disposed at least partially within said open center of said annulus of said capacitor.

4. The implantable cardiac stimulator of claim 2, in which said control circuitry is disposed at least partially within said open center of said annulus of said capacitor.

5. The implantable cardiac stimulator of claim 2, wherein said annulus is generally elliptical.

6. The implantable cardiac stimulator of claim 5, in which said battery is generally elliptical and is disposed at least partially within said open center of said annulus of said capacitor.

7. The implantable cardiac stimulator of claim 3, and further including a circuit board, in which said capacitor and said battery are disposed in a first common plane, and at least a portion of said control circuitry is disposed on said circuit board, said circuit board being disposed in a second plane substantially parallel to the first plane.

8. The implantable cardiac stimulator of claim 2, and further including a second energy storage capacitor disposed within said housing and disposed at least partially within said open center of said annulus of said capacitor.

9. The implantable cardiac stimulator of claim 8, in which said second energy storage capacitor is itself constructed as an annulus having an open center.

10. The implantable cardiac stimulator of claim 9, in which said battery is disposed at least partially within said open center of said annulus of said second storage capacitor.

11. An implantable cardiac stimulator comprising:
a housing having mutually orthogonal thickness, width and length axes, said housing having a thickness dimension measured along said thickness axis, a width dimension measured along said width axis and a length dimension measured along said length axis, wherein said thickness dimension is smaller than either of said width and length dimensions;
an electrical contact attached to said housing;
a battery;
an energy storage capacitor; and
control circuitry electrically connected to said contact, battery and capacitor;
said battery, capacitor and control circuitry being disposed within said housing;
said energy storage capacitor having mutually orthogonal thickness, width and length axes, and having a thickness dimension measured along said thickness axis, a width dimension measured along said width axis and a length dimension measured along said length axis, wherein said thickness dimension of said capacitor is smaller than either of said width and length dimensions of said capacitor, said capacitor further including a first plate layer, a second plate layer, and a dielectric layer separating said first plate layer and said second plate layer, said first plate, second plate and dielectric layers being arranged spirally about an axis parallel to said thickness axis of said capacitor, said thickness axis of said capacitor being substantially parallel to said thickness axis of said housing.

12. The implantable cardiac stimulator of claim 11, wherein said first plate, second plate and dielectric layers are generally arranged as an annulus having an open center.

13. The implantable cardiac stimulator of claim 12, in which said battery is disposed at least partially within said open center of said annulus of said capacitor.

14. The implantable cardiac stimulator of claim 12, in which said control circuitry is disposed at least partially within said open center of said annulus of said capacitor.

15. The implantable cardiac stimulator of claim 12, wherein said annulus is generally elliptical.

16. The implantable cardiac stimulator of claim 15, in which said battery is generally elliptical and is disposed at least partially within said open center of said annulus of said capacitor.

17. The implantable cardiac stimulator of claim 13, and further including a circuit board, in which said capacitor and said battery are disposed in a first common plane, and at least a portion of said control circuitry is disposed on said circuit board, said circuit board being that is disposed in a second plane substantially parallel to the first plane.

18. The implantable cardiac stimulator of claim 12, and further including a second energy storage capacitor disposed within said housing and disposed at least partially within said open center of said annulus of said capacitor.

19. The implantable cardiac stimulator of claim 18, in which said second energy storage capacitor is itself constructed as an annulus having an open center.

20. The implantable cardiac stimulator of claim 19, in which said battery is disposed at least partially within said open center of said annulus of said second storage capacitor.

* * * * *